(12) United States Patent
Gondi et al.

(10) Patent No.: US 10,597,355 B2
(45) Date of Patent: Mar. 24, 2020

(54) 1,1-DISUBSTITUTED ETHYLENE PROCESS

(71) Applicant: OptMed, Inc., New York, NY (US)

(72) Inventors: Vijaya Bhasker Gondi, Burlington, MA (US); John Gregory Reid, Groton, MA (US)

(73) Assignee: OptMed, Inc., New York, NY (US)

( * ) Notice: Subject to any disclaimer, the term of this patent is extended or adjusted under 35 U.S.C. 154(b) by 1247 days.

(21) Appl. No.: 14/628,273

(22) Filed: Feb. 22, 2015

(65) Prior Publication Data

US 2015/0166471 A1  Jun. 18, 2015

Related U.S. Application Data

(63) Continuation of application No. 13/752,384, filed on Jan. 28, 2013, now abandoned.

(60) Provisional application No. 61/591,884, filed on Jan. 28, 2012.

(51) Int. Cl.
*C07C 253/30* (2006.01)
*C07C 67/317* (2006.01)
*C07C 67/343* (2006.01)

(52) U.S. Cl.
CPC .......... *C07C 253/30* (2013.01); *C07C 67/317* (2013.01); *C07C 67/343* (2013.01)

(58) Field of Classification Search
CPC ........................... C07C 67/317; C07C 67/343
See application file for complete search history.

(56) References Cited

U.S. PATENT DOCUMENTS

| | | | |
|---|---|---|---|
| 4,049,698 | A  | 9/1977  | Hawkins et al. |
| 6,894,184 | B2 | 5/2005  | Hachtel et al. |
| 7,569,719 | B1 | 8/2009  | McArdle et al. |
| 7,659,423 | B1 | 2/2010  | McArdle et al. |
| 7,718,821 | B1 | 5/2010  | Bigi et al. |
| 7,973,119 | B1 | 7/2011  | McArdle et al. |
| 8,022,251 | B2 | 9/2011  | McArdle et al. |
| 9,841,640 | B2 | 12/2017 | Song et al. |
| 2010/0199888 | A1 | 8/2010 | McArdle et al. |
| 2010/0210788 | A1 | 8/2010 | McArdle et al. |

OTHER PUBLICATIONS

Ates et. al. "Trifluorethylidenation of Compounds with Activated Methylene Groups," Tetrahedron Letters, vol. 34, No. 36, pp. 5711-5714, 1993.
Vogel's Textbook of Quantitative Chemical Analysis, Jeffery et. al. Ed, 5th Edition, Chpt. 8, pp. 216-220.
Mohrle et. al., "Aminomethyllierung von 1,3-Diketonen", Pharmazie 40, pp. 697-701, 1985.

*Primary Examiner* — Ana Z Muresan
(74) *Attorney, Agent, or Firm* — IP&L Solutions; Edward K Welch, II

(57) ABSTRACT

Improved iminium based processes for the production of cyanoacrylates and methylidene malonates wherein the improvement pertains to the presence of acid chlorides and/or acid anhydrides in the reaction mix.

10 Claims, No Drawings

1,1-DISUBSTITUTED ETHYLENE PROCESS

RELATED APPLICATION

This patent application is a continuation of U.S. application Ser. No. 13/752,384 filed Jan. 28, 2013 which claims the benefit of prior U.S. Provisional Patent Application No. 61/591,884 filed Jan. 28, 2012, entitled Improved Methylidene Malonate Process, Gondi et. al., the contents of both of which are hereby incorporated herein in their entirety.

FIELD OF THE INVENTION

The present invention relates to a process for improving cure speed and/or providing more consistent, i.e., batch-to-batch, cure speed in 1,1-disubstituted ethylene monomers and monomer containing compositions. The present invention also relates to an improved process for the production of 1,1-disubstituted ethylene monomers, including methylidene malonates and cyanoacrylates, especially methylidene malonates, and the use thereof.

BACKGROUND 1,1-disubstituted ethylene monomers and compositions containing the same are well known and, for the most part, widely available. They have utility in a broad array of end-use applications, most notably those which take advantage of their cure or polymerizable properties. Specifically, they find broad utility in coatings, sealants and adhesives, among other applications. Those 1,1-disubstituted ethylenes having one or, preferably, two electron withdrawing substituents at the 1 position have been used to provide adhesives and sealants with rapid cure rates and high bond strengths. Most notable among these are the cyanoacrylates such as ethyl cyanoacrylate and butyl cyanoacrylate. Another class of 1,1-disubstituted ethylenes that have demonstrated a lot of promise, but have limited, if any, commercial success are the methylidene malonates, including diethyl methylidene malonate.

Commercial success of the 1,1-disubstituted ethylenes is reliant upon a number of variables and factors including reasonable cost, high purity, good, especially long, shelf life and rapid cure rate. In an effort to achieve these goals, much work has been done to develop new and/or improved processes and synthetic schemes for their manufacture, purification and isolation.

For example, α-cyano acrylates have been prepared (U.S. Pat. No. 6,245,933) by reacting a cyanoacetate such as ethyl cyanoacetate with formaldehyde or a formaldehyde synthon such as paraformaldehyde in a Knoevenagel condensation followed by transesterification. The product mixture is then cracked and distilled to produce the α-cyano acrylate monomer.

Similarly, extensive efforts have been undertaken over many decades in an effort to produce, on a commercially viable basis, methylidene malonates. Two of the earliest methods for the production of dialkyl methylidene malonates, the simplest of the methylidene malonates, were the iodide method in which methylene iodide was reacted with dialkyl malonates and the formaldehyde method in which formaldehyde was reacted with dialkyl malonates in the presence of a base, in solution in alcohol solvents. As an alternative, Bachman et al. (U.S. Pat. No. 2,313,501) taught the reaction of a $C_1$-$C_5$ dialkyl malonate with formaldehyde in the presence of an alkali metal salt of a carboxylic acid, in solution in a substantially anhydrous carboxylic acid solvent, followed by fractional distillation to separate the desired product. D'Alelio (U.S. Pat. No. 2,330,033), on the other hand, alleged that such processes were erratic and more often produced yields that averaged 10 to 12 percent. D'Alelio espoused an improved process with yields on the order of 30% and higher by reacting a malonic acid ester with formaldehyde in a ratio of one mole of the former to at least one mole of the latter under alkaline conditions and, in most cases, in the presence of a polymerization inhibitor such as copper, copper acetate, hydroquinone, resorcinol, or catechol, to form a methylol derivative. The methylol derivative was then acidified to a pH below 7.0 using a suitable organic or inorganic acid in order to retard further reaction. The acidified mass is then dehydrated to form the corresponding methylidene malonate which is subsequently separated by distillation.

Not satisfied, Coover et al. (U.S. Pat. Nos. 3,221,745 and 3,523,097) took yet another approach to the formation of the methylidene malonates, electing to begin with a preformed dialkyl alkoxymethylenemalonate. In accordance with their process, the olefinic double bond of the latter compound was subjected to hydrogenation in the presence of a hydrogenation catalyst and the hydrogenated compound was then subject to pyrolysis in the presence of a phosphorous pentoxide inhibitor to strip off the alcohol to produce the methylene malonate. The resultant mass was then subjected to vacuum distillation at low temperature to separate an allegedly high purity methylidene malonate, though with a low yield. According to Coover et al., the use of low temperature distillation is said to prevent the contamination of the monomer with pyrolytic products that commonly result from high temperature distillation. These high purity monomers are said to be especially important for surgical applications.

Eventually, such efforts led to multi-step processes in which certain unsaturated molecules served as a platform for the formation of intermediate adducts from which the methylidene malonates were subsequently stripped and recovered. For example, Hawkins et al. (U.S. Pat. No. 4,049,698) found that certain malonic diesters could be reacted with formaldehyde and a linear, conjugated diene in the presence of a primary, secondary or tertiary amine at about reflux temperature to form an intermediate adduct that could then be readily pyrolyzed at temperatures in excess of 600° C. to split off the desired methylidene malonate. Similarly, Ponticello (U.S. Pat. No. 4,056,543) and Ponticello et al. (U.S. Pat. No. 4,160,864) developed processes by which asymmetrical methylene malonates, especially methyl allyl methylene malonate, were prepared from previously formed norbornene adducts, the latter having been prepared by the Diels-Alder reaction of an alkyl acrylate with cyclopentadiene at room temperature or with heating or use of a Lewis catalyst. The so formed monoester norbornene adducts were then reacted with an electrophile material in the presence of an alkyl-substituted lithium amide complex to form the diester adduct and subsequently pyrolyzed at a temperature of 400° C. to 800° C. at a pressure of 1 mm to 760 mm Hg in an inert atmosphere to strip off the desired methylene malonates.

Citing numerous disadvantages of the foregoing processes, which disadvantages were said to make them difficult, if not impossible, to adapt to industrial scale, Bru-Magniez et al. (U.S. Pat. Nos. 4,932,584 and 5,142,098) developed a process whereby anthracene adducts were prepared by reacting mono- or di-malonic acid ester with formaldehyde in the presence of anthracene, most preferably in a non-aqueous solvent medium in the presence of select catalysts. According to Bru-Magniez et al., the anthracene adducts were said to be readily produced in high yields with the desired methylidene malonates obtained by stripping them from the anthracene adduct by any of the known methods including heat treatment, thermolysis, pyrolysis or hydrolysis; preferably heat treatment in the presence of maleic anhydride.

Despite all of these efforts, issues remained and commercial success wanting owing to continued process frustrations, instability and unpredictability. Malofsky et al. (WO 2010/129068) solved some of the problems associated with process instability of the Retro-Diels-Alder adduct process by using polymerization inhibitors concurrent with or prior to stripping the adduct. Inhibitors such as trifluoroacetic acid and hydroquinone were used. In some examples, trifluoroacetic acid was also added to the distillate. Only limited curing studies were done, but the resultant malonates were able to be polymerized with tetrabutylammonium fluoride. Malofsky teaches a variety of purification processes including double distillation and extracting the product with an alkane such as n-heptane. Although this is an improvement over the art, these various purification processes can be costly and can reduce yield.

More recently, in an effort to find alternate and better routes to producing 1,1-disubstituted ethylenes, a focus has been directed to certain iminium based processes wherein select iminium salts are reacted with various compounds containing a methylene linkage having attached thereto at least one electron withdrawing group selected from nitriles, carboxylic acids, carboxylic esters, sulphonic acids, ketones or nitro to form electron deficient olefins. For example, McArdle et al. (WO 2008/050313, U.S. Pat. App. Pub. 2009/0203934, and U.S. Pat. No. 8,022,251) have taught the use certain specific iminium salts having a tertiary carbon atom attached to a nitrogen atom in the production of electron deficient olefins, most especially cyanoacrylates, however, methylidene malonates are also mentioned. The preferred process involved employing the select iminium salts in producing the 2-cyanoacrylates from nitriles such as ethyl cyanoacetate or malonitrile. When a formaldehyde derivative is used, the McArdle iminium salt can have the structure I:

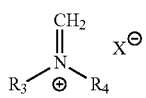

I wherein $R_3$ is H, alkenyl, or alkynyl; $R_4$ is a hydrocarbon moiety comprising a tertiary carbon which is attached to the N atom, where the tertiary carbon atom is attached to or a part of one or more substituents selected from linear, branched, or cyclic alkyl or alkenyl, or one or more together form a cyclic structure; and X is an anion such as a non-nucleophilic and/or an acidic anion. These imines may be formed by reacting formaldehyde or a source thereof with a primary amine having a tertiary carbon atom attached to the nitrogen to form an imine which is subsequently reacted with an acid under specified conditions to yield an iminium salt. Variations and refinements of the iminium process are taught in McArdle et al. (U.S. Pat. Nos. 7,659,423 and 7,973,119 and U.S. Pat. App. Pub. Nos. 2010/0210788 and 2010/0199888) and Bigi et al. (U.S. Pat. No. 7,718,821); the contents of all of which are hereby incorporated herein by reference.

The McArdle et. al. and Bigi et. al. iminium processes are not without their shortcomings. Both require high temperature reactions, temperatures which can promote the in-situ polymerization of the monomer product. Additionally, these processes require specific amines to form the iminium salts: amines that are oftentimes expensive and whose reaction byproducts are found, particularly in the case of methylidene malonates, to promote unwanted reactions in-situ, including, specifically dimerization of the monomer. Further, these processes must be conducted at a very low pH in order to prevent the retro-conversion of the iminium salt back to the imine by loss of a proton. From the perspective of the formation of cyanoacrylate monomers, these factors are of low concern, if any, as traditional processes for the production of cyanoacrylates involves the formation of the polymer which is then cracked, typically at high temperature, to form the monomer and have other issues that they too must content with. However, from the perspective of the formation of methylidene malonates, these factors are of considerable concern, particularly inasmuch as the yields and purity of the methylidene malonates so produced, as shown by McArdle et. al., are still low.

Thus, despite the advances that have been made, there are still improvements to be made. More importantly, there still remains a need for a commercially viable process for the production and isolation of methylidene malonates: a process which balances simplicity of process with common or at least less costly materials with high yields and purity and with consistency and repeatability.

SUMMARY OF THE INVENTION

The present invention provides for new and/or improved processes for the production of 1,1-disubstituted ethylenes, particularly methylidene malonates and cyanoacrylates, most especially the methylidene malonates, and for the purification and isolation thereof as well as for the 1,1-disubstituted ethylenes formed thereby. Each of these processes presents an improvement over existing iminium processes and produces 1,1-disubstituted ethylenes quickly and efficiently in high yield and purity and at relatively low cost, particularly as compared to non-iminium processes and even certain known iminium processes.

According to a first aspect of the present teachings there is provided a method of producing 1,1-disubstituted ethylenes which method comprises reacting compounds containing a methylene linkage having attached thereto at least one electron withdrawing group, especially those selected from nitriles, carboxylic acids, carboxylic esters, sulphonic acids, ketones or nitro, most especially the esters, especially the diesters, of malonic acid, with an iminium salt in the presence of an acid chloride and/or acid anhydride under appropriate conditions and for an appropriate time period to yield the corresponding 1,1-disubstituted ethylene. The iminium salts may be a pre-formed, isolated and/or purified iminium salt or it may be an iminium salt that is formed in-situ by a process that is integrated into the overall reaction process for the production of the 1,1-disubstituted ethylene. In the latter case, depending upon the specific iminium salt and its reactants and reaction products, it is possible to directly combine the compound containing the methylene linkage with the reaction product of the iminium reaction process, a product which, it is believed, inherently contains the iminium salt.

Suitable iminium salts generally correspond to the formula II

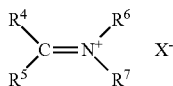

wherein $R^4$, $R^5$, $R^6$ and $R^7$ are each independently H or a hydrocarbon or substituted hydrocarbon moiety or a hydrocarbon, substituted hydrocarbon or heterohydrocarbon bridge whereby the nitrogen atom, the carbon, or both of formula II are in a ring structure, preferably, $R^4$, $R^5$, $R^6$ and $R^7$ are each independently H or an alkyl, aryl, alkenyl or alkynyl, and X is an anion, preferably a halogen, a non-nucleophilic anion, and/or a conjugate base of an acid, most preferably a halogen, a carboxylate or a sulfonate. This process may be performed in the presence of a polar or non-polar solvent or in a solvent-free process.

Preferred iminium salts are those wherein $R^4$ and $R^5$ are hydrogen (H) and $R^6$ and $R^7$ are each independently a hydrocarbon or substituted hydrocarbon moiety, especially an alkyl, aryl, alkenyl or alkynyl moiety, most especially an alkyl moiety, and X is a halogen or a substituted or unsubstituted carboxylate. In those instances where $R^6$ and/or $R^7$ have a tertiary carbon atom attached to the nitrogen atom of the iminium salt, it is preferred that such be used in producing 1,1-disubstituted ethylenes other than the methylidene malonates, particularly the cyanoacrylates: though again, they are suitable for the methylidene malonates as well. Especially preferred iminium salts are those wherein $R^4$ and $R^5$ are hydrogen or alkyl, and both $R^6$ and $R^7$ are hydrocarbon moieties, especially alkyl. Most preferred are the dialkylmethylideneammonium halides and carboxylates, particularly the dialkyl methylideneammonium chlorides, acetates and haloacetates. For purposes of clarity, "alkyidene" refers to that portion of the iminium compound comprising:

Thus, an iminium compound wherein $R^4$ and $R^5$ are H and $R^6$ and $R^7$ are methyl would be referred to as a dimethylmethylidene ammonium compound.

According to a second and preferred aspect of the present teachings there is provided a method of producing 1,1-disubstituted ethylenes which method comprises reacting an amine with an acid chloride and/or an acid anhydride, preferably at an equivalent excess of acid chloride and/or acid anhydride relative to the methylene containing compound, to form an iminium reaction product, typically comprising an iminium salt, and then reacting that reaction product, with or without isolation or purification. with a compound containing a methylene linkage having attached thereto at least one electron withdrawing group selected from nitriles, carboxylic acids, carboxylic esters, sulphonic acids, ketones or nitro, most especially the esters, especially the diesters, of malonic acid, under appropriate conditions and for an appropriate time period to yield the corresponding 1,1-disubstituted ethylene. This process too may be performed in the presence of a polar or non-polar solvent or in a solvent-free process.

According to a third aspect of the present teachings there is provided a method of producing 1,1-disubstituted ethylenes which method comprises reacting compounds containing a methylene linkage having attached thereto at least one electron withdrawing group selected from nitriles, carboxylic acids, carboxylic esters, sulphonic acids, ketones or nitro, most especially the esters, especially the diesters, of malonic acid, with an iminium salt or an iminium reaction product in the presence of a non-polar solvent for a sufficient time to yield the corresponding 1,1-disubstituted ethylene wherein the anionic portion of the iminium compound or in-situ formed iminium reaction product is or is prepared from a carboxylate or an anhydride.

According to a fourth aspect of the present teachings there is provided an improved method of producing 1,1-disubstituted ethylenes involving the reaction of compounds containing a methylene linkage having attached thereto at least one electron withdrawing group selected from nitriles, carboxylic acids, carboxylic esters, sulphonic acids, ketones or nitro, most especially the esters, especially the diesters, of malonic acid, with an iminium salt or an iminium reaction product wherein the improvement comprises treating the 1,1-disubstituted ethylenic reaction product with a solid phase material known to adsorb or absorb polar materials in the presence of a non-polar solvent following completion of the reaction. If the reaction process to form the 1,1-disubstituted ethylene is conducted in the presence of a polar solvent, one must first remove and replace the polar solvent with a non-polar solvent. Treatment with the solid phase material is continued until most, if not substantially all, of the polar impurities are absorbed or adsorbed, after which the reaction product is then isolated/separated from the solid phase material, e.g., by filtration, centrifugation, decanting, distillation, thin film evaporation, etc. Suitable solid phase materials include ion-exchange resins, molecular sieves, zeolites, alumina, and the like, provided that the same are acidic to neutral pH, preferably acidic.

According to yet a fifth aspect of the present teachings there is provided an improved method of producing 1,1-disubstituted ethylenes involving the reaction of compounds containing a methylene linkage having attached thereto at least one electron withdrawing group selected from nitriles, carboxylic acids, carboxylic esters, sulphonic acids, ketones or nitro, most especially the esters, especially the diesters, of malonic acid, with an iminium salt or an iminium reaction product wherein the improvement comprises treating the isolated and/or purified 1,1-disubstituted ethylene with a slightly acidic to mildly basic alumina and thereafter separating the alumina from the treated 1,1-disubstituted ethylene.

Finally, it is also to be appreciated that the present teachings provide further improvements in relation to the foregoing methods, whereby the further improvement lies in the practice of two or more of the aforementioned processes in a single process for the production of 1,1-disubstituted ethylenes.

DETAILED DESCRIPTION

In accordance with the present teachings there are provided new and/or improved processes or methods for the production of methylidene malonates. All of these processes generally comprise the reaction of a compound containing a methylene linkage having attached thereto at least one electron withdrawing group with a preformed or in-situ formed iminium salt. As will be noted, there are several various processes and improvements to existing processes disclosed herein that may be used individually or in combination, e.g., the improvements to existing methods are also applicable to improve the new methods taught herein.

For purposes of convenience and expediency, unless otherwise obvious from the text, the term "ethylene precursor" shall refer to the compounds containing the methylene linkage having attached thereto the one or more electron withdrawing groups. Similarly, unless context disallows, reference to the "iminium salt" shall refer to both a preformed iminium salt as well as the in-situ formed salt, whether in a purified or isolated state or as the reaction product of the reactants therefore.

According to a first aspect of the present teachings there is provided a method of producing 1,1-disubstituted ethylenes which method comprises reacting ethylene precursors with an iminium salt in the presence of an acid chloride and/or acid anhydride under appropriate conditions, and preferably in the presence of a polar or non-polar solvent, and for an appropriate time period to yield the corresponding 1,1-disubstituted ethylene.

According to a second and preferred aspect of the present teachings there is provided a method of producing 1,1-disubstituted ethylenes which method comprises reacting an amine with an acid chloride and/or an acid anhydride, preferably at an equivalent excess of acid chloride and/or acid anhydride relative to the methylene containing compound, to form an iminium reaction product, typically comprising an iminium salt, and then reacting that reaction product, with or without isolation or purification, with an ethylene precursor under appropriate conditions and for an appropriate time period to yield the corresponding 1,1-disubstituted ethylene. Each of the process steps of this second aspect of the present teachings is preferably conducted in the presence of a solvent, which may be polar or non-polar.

According to a third aspect of the present teachings there is provided a method of producing 1,1-disubstituted ethylenes which method comprises reacting an ethylene precursor with an iminium salt or an iminium reaction product in the presence of a non-polar solvent for a sufficient time to yield the corresponding 1,1-disubstituted ethylene wherein the anionic portion of the iminium compound or in-situ formed iminium reaction product is or is prepared from a substituted or unsubstituted carboxylate or anhydride.

According to a fourth aspect of the present teachings there is provided an improved method of producing 1,1-disubstituted ethylenes involving the reaction of an ethylene precursor with an iminium salt wherein the improvement comprises treating the 1,1-disubstituted ethylenic reaction product with a solid phase material known to adsorb or absorb polar materials in the presence of a non-polar solvent following completion of the reaction. If the reaction process to form the 1,1-disubstituted ethylene is conducted in the presence of a polar solvent, one must first remove and replace the polar solvent with a non-polar solvent. Treatment with the solid phase material is continued until most, if not substantially all, of the polar impurities are absorbed or adsorbed, after which the reaction product is then isolated/separated from the solid phase material, e.g., by filtration, centrifugation, decanting, distillation, thin film evaporation, etc. Suitable solid phase materials include ion-exchange resins, molecular sieves, zeolites, alumina, and the like, provided that the same are acidic to neutral pH, preferably acidic.

According to yet a fifth aspect of the present teachings there is provided an improved method of producing 1,1-disubstituted ethylenes involving the reaction of an ethylene precursor with an iminium salt wherein the improvement comprises treating the isolated and/or purified 1,1-disubstituted ethylene with a slightly acidic to mildly basic alumina and thereafter separating the alumina from the treated 1,1-disubstituted ethylene.

In its most broad concept, the present teachings apply to the production of 1,1-disubstituted ethylenes having at least one electron withdrawing substituent at the one position with the preferred electron withdrawing groups being selected from nitriles (including cyano), nitro, carboxylic acids, carboxylic acid esters, sulphonic acids and esters, amides, ketones and formyl, especially cyano and carboxylic acid esters. Such 1,1-disubstituted ethylenes generally correspond to the general formula III:

wherein R is H or $C_1$ to $C_6$ hydrocarbyl such as methyl, ethyl, ethenyl, propyl, propenyl, isopropyl, ispropenyl, butyl, or phenyl and X and Y are independently selected from $C_1$ to $C_{12}$, preferably $C_1$ to $C_{10}$, most preferably $C_2$ to $C_8$, hydrocarbyl or heterohydrocarbyl groups provided that at least one of X and Y is a strong electron withdrawing group. Exemplary strong electron withdrawing groups include, but are not limited to, cyano, carboxylic acid, carboxylic acid esters, amides, ketones or formyl and Y is cyano, carboxylic acid, carboxylic acid esters, amides, ketones, sulfinates, sulfonates, or formyl. Monomers within the scope of Formula I include α-cyanoacrylates, vinylidene cyanides, alkyl homologues of vinylidene cyanide, methylidene malonates, dialkyl methylene malonates, acylacrylonitriles, vinyl sulfinates, and vinyl sulfonates.

Exemplary preferred 1,1-disubstituted ethylene monomers of formula I include, but are not limited to:

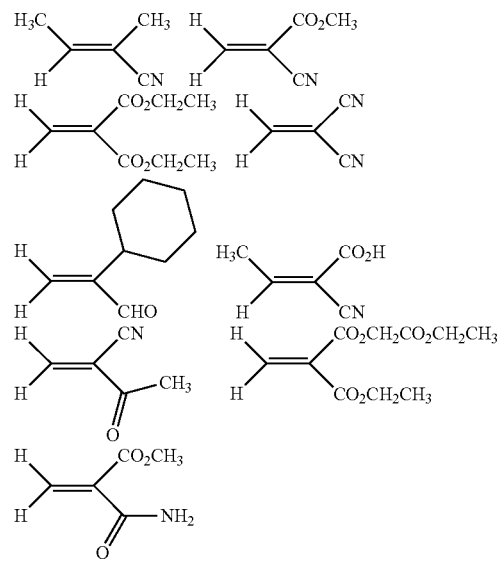

$H_2C$=$C(CN)CO_2CH_2CH_3$, $H_2C$=$C(CN)CO_2(CH_2)_3CH_3$, $H_2C$=$C(CN)CO_2(CH_2)_5CH_3$ and $H_2C$=$C(CN)CO_2(CH_2)_7CH_3$.

Exemplary preferred 1,1-disubstituted ethylene monomers are those of the formula IV:

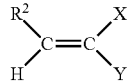
                                                    IV where $R^2$ is H or —CH=CH$_2$, most preferably H; and X and Y are each independently —CN or —COOR$^3$ wherein $R^3$ is:

a hydrocarbyl or substituted hydrocarbyl group;

a group having the formula —R$^4$—O—R$^5$—O—R$^6$, wherein $R^4$ is a 1,2-alkylene group having 2-4 carbon atoms, $R^5$ is an alkylene group having 2-4 carbon atoms, and $R^6$ is an alkyl group having 1-6 carbon atoms; or a group having the formula

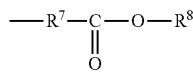

wherein $R^1$ is —(CH$_2$)$_n$—; —CH(CH$_3$)—; or —C(CH$_3$)$_2$— wherein n is 1 to 10, preferably 1-5, and $R^8$ is H or an organic moiety, preferably a hydrocarbyl or substituted hydrocarbyl. Suitable hydrocarbyl and substituted hydrocarbyl groups include, but are not limited to, C$_1$-C$_{16}$, preferably C$_1$-C$_8$, straight chain or branched chain alkyl groups; C$_1$-C$_{16}$, preferably C$_1$-C$_8$, straight chain or branched chain alkyl groups substituted with an acyloxy group, a haloalkyl group, an alkoxy group, a halogen atom, a cyano group, or a haloalkyl group; C$_2$-C$_{16}$, preferably C$_2$-C$_8$, straight chain or branched chain alkenyl groups; C$_2$-C$_{12}$, preferably C$_2$-C$_8$, straight chain or branched chain alkynyl groups; and C$_3$-C$_{16}$, preferably C$_3$-C$_8$, cycloalkyl groups; as well as aryl and substituted aryl groups such as phenyl and substituted phenyl and aralkyl groups such as benzyl, methylbenzyl, and phenylethyl. Substituted hydrocarbyl groups include halogen substituted hydrocarbons such as chloro-, fluoro- and bromo-substituted hydrocarbons and oxy-substituted hydrocarbons such as alkoxy substituted hydrocarbons.

Those skilled in the art will readily appreciate the ethylene precursors, i.e., the compounds containing a methylene linkage and having attached thereto at least one electron withdrawing group, necessary to produce the desired 1,1-disubstituted ethylene as described above. Exemplary electron withdrawing groups include nitriles (including cyano), nitro, carboxylic acids, carboxylic acid esters, sulphonic acids and esters, amides, ketones and formyl. Preferred ethylene precursors are those compounds having two or more electron withdrawing groups, wherein the electron withdrawing groups may be the same or different, for example, the ethylene precursor will have both a nitrile and carboxylic acid ester withdrawing groups in the case of the production of cyanoacrylate monomers.

Representative ethylene precursors include the malonitrile, malonic acid and its esters (including, particularly, its diesters), cyanoacetic acid and its esters (including, especially, the alkyl substituted acids and esters, e.g., ethylcyanoacetate, butylcyanoacetate, octylcyanoacetate, etc.), ethyl nitro acetate, Meldrum's acid and the like.

The present teachings are especially applicable to the reaction of the iminium salts with the cyanoacetates and the malonic acid esters. The former generally correspond to the formula V and the latter to the formula VI:

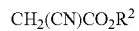
                                                    V

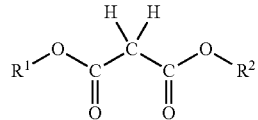
                                                    VI wherein, $R^1$ is H in the case of the mono-esters; otherwise $R^1$ and $R^2$ are each independently a C$_1$ to C$_{18}$, preferably C$_1$ to C$_{12}$, more preferably C$_1$ to C$_6$, hydrocarbon or heterohydrocarbon group, the latter having one or more nitrogen, halogen, or oxygen atoms.

Preferably, $R^2$ is a C$_2$ to C$_8$ alkyl group in the case of the cyanoacetate. However, for many of the other ethylene precursors, especially the malonate esters, $R^1$ and $R^2$ are, preferably, both hydrocarbon and/or heterohydrocarbon groups and represent a C$_1$ to C$_{10}$, more preferably a C$_1$ to C$_6$, linear or branched alkyl group; a C$_3$ to C$_8$ alicyclic group; a C$_2$ to C$_6$ alkenyl group; or a C$_2$ to C$_6$ alkynyl group, either or both of which may be substituted with an ether, epoxide, halo, ester, cyano, aldehyde, keto or aryl group. Most preferably, both $R^1$ and $R^2$ are hydrocarbon or heterohydrocarbon groups wherein at least one contains an ester linkage. In this regard, especially desirable diesters of malonic acid are those wherein at least one of the $R^1$ and $R^2$ groups is of the formula:

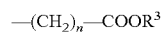

wherein $R^3$ is a C$_1$ to C$_{17}$, preferably a C$_1$ to C$_6$ hydrocarbon or heterohydrocarbon group, the latter having one or more nitrogen, halogen, or oxygen atoms. Preferably, $R^3$ is a C$_1$ to C$_6$, preferably a C$_1$ to C$_3$, lower alkyl and n is an integer of from 1 to 5, preferably 1 or 2.

Exemplary diesters of malonic acid include dimethyl malonate, diethylmalonate, di-isopropyl malonate, di-n-propyl malonate, and ethyl methyl malonate as well as those of the formula:

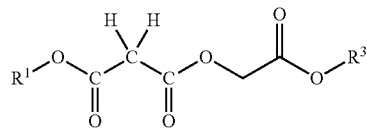

wherein $R^1$ and $R^3$ are the same or different and represent a C$_1$ to C$_3$ lower alkyl, especially ethyl.

The second critical reactant for the production of the 1,1-disubstituted ethylenes is the iminium. As noted above, these may be a pre-formed and/or isolated and/or purified iminium salts or it may be present as an iminium salt or iminium salt reaction mix that is formed in-situ by a process that is integrated into the overall reaction process for the production of the 1,1-disubstituted ethylene. In the latter case, depending upon the specific iminium salt and its reactants and reaction products, it is possible to directly combine the ethylene precursor with the reaction product of the iminium reaction process, a product which, it is believed, inherently contains the iminium salt.

Suitable iminium salts generally correspond to the formula II

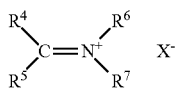

wherein $R^4$, $R^5$, $R^6$ and $R^7$ are each independently H or a hydrocarbon or substituted hydrocarbon moiety or a hydrocarbon, substituted hydrocarbon or heterohydrocarbon bridge whereby the nitrogen atom, the carbon, or both of formula II are in a ring structure, preferably, $R^4$, $R^5$, $R^6$ and $R^7$ are each independently H or an alkyl, aryl, alkenyl or alkynyl; and X is an anion, preferably a halogen, a non-nucleophilic anion, and/or the conjugate salt of an acid, most preferably a halogen, a carboxylate or a sulfonate. Generally speaking, if a hydrocarbon or heterohydrocarbon moiety, $R^4$, $R^5$, $R^6$ and $R^7$ will have from 1 to 10, preferably from 1 to 6 carbon atoms. Preferably, $R^4$, $R^5$, $R^6$ and $R^7$ are each independently H or an alkyl, aryl, alkenyl or alkynyl, most preferably alkyl. X is an anion, preferably a halogen, a non-nucleophilic anion, and/or the conjugate base of an acid, most preferably a halogen, a carboxylate or a sulfonate. In those instances where $R^6$ and/or $R^7$ have a tertiary carbon atom attached to the nitrogen atom of the iminium salt, it is preferred that such be used in producing 1,1-disubstituted ethylenes other than the methylidene malonates, particularly the cyanoacrylates: though again, they are suitable for the methylidene malonates as well.

A group of preferred iminium salts are those wherein $R^4$ and $R^5$ are both hydrogen H and $R^6$ and $R^7$ are both H or at least one is H and the other a hydrocarbon or substituted hydrocarbon moiety, especially an alkyl, aryl, alkenyl or alkynyl moiety, most especially an alkyl moiety, and X is a halogen or a substituted or unsubstituted carboxylate. Especially preferred iminium salts are those wherein $R^4$ and $R^5$ are hydrogen or alkyl, most preferably H or a $C_1$ to $C_6$ lower alkyl, and $R^6$ and $R^7$ are each independently a hydrocarbon or substituted hydrocarbon moiety, especially an alkyl, aryl alkenyl or alkynyl moiety, most especially a $C_1$ to $C_6$ lower alkyl, and X is a halogen or a substituted or unsubstituted carboxylate. Most preferred are the dialkylalkylideneammonium halides and carboxylates, particularly the dialkylalkylideneammonium chlorides, acetates and haloacetates. For purposes of clarity, "alkyidene" refers to that portion of the iminium compound comprising:

Thus, an iminium compound wherein $R^4$ and $R^5$ are H and $R^6$ and $R^7$ are methyl would be referred to as a dimethylmethylidene ammonium compound.

The iminium salts may be formed by a number of alternative processes, all of which are well known in the art. One general route by which they may be formed involves the preparation of the iminium salt from the corresponding imine, which process may further involve the formation of the imine from select amines. Such processes are described in, e.g., Abbaspour Tehrani and De Kimpe, Science of Synthesis, 27, 313 (2004), and references cited therein; Jahn and Schroth, Tett. Lett., 34(37), 5863 (1993); M. B. Smith, Organic Synthesis, McGraw Hill International, Chemistry Series, 1302 (1994) and references cited therein; Hin, B., Majer, P., Tsukamoto, T., J. Org. Chem., 67, 7365 (2002)] and in Mannich reactions [Holy et al, Tetrahedron, 35, 613 (1979); Bryson et al, J. Org. Chem., 45, 524 (1980); and McArdle et. al., U.S. Pat. No. 7,569,719, all of which are incorporated herein by reference in their entirety.

Generally speaking, the iminium salts (also in the past referred to as immonium salts) may be methanimimium salts, derived from formaldehyde; ternary iminium salts derived from aldehydes, e.g., acrolein; and quaternary iminium salts derived from ketones. Their preparations may be conducted with or without added catalyst provided that when a catalyst is added, the catalyst should be one that is not solely a basic nucleophile. Thus, an acidic system would be preferred and a ditropic system may be used, as well.

Typically the imines from which the iminium salts are formed are produced through the reaction of a carbonyl compound, especially an aldehyde, and an amine, such as a primary amine like aniline, N-methylamine, or N-propylamine, which reaction results in the removal of water. Desirably, when a primary amine is used, the primary amine should be one with some degree of steric hindrance, such as tertiary butyl amine. The reaction of primary amine with carbonyl compound is well known and can be a facile, high yielding reaction that may be conducted on a commercial scale e.g., see U.S. Pat. Nos. 2,582,128 and 5,744,642, both of which are hereby incorporated herein by reference.

The so-formed imines from primary amines may be converted into iminium salts by contacting them with an acidic species, such as trifluoroacetic acid, acetic acid, sulphuric acid, methane sulfonic acid, or camphor sulfonic acid, and the like.

Another route to preparing the iminium salts is the use of secondary amines wherein a secondary amine, such as dimethylamine, pyrrolidine, morpholine, and the like, are first converted to their respective salts and then reacted with the carbonyl compound (with the removal of water) to produce iminium salts. Alternatively, the iminium salts can be formed by the reaction of chloromethyl ethers with N-(trimethylsilyl)amines. See e.g. Jahn and Schroth, Tett. Lett., 34(37), 5863 (1993) and Abbaspour Tehrani and De Kimpe, Science of Synthesis, 27, 313 (2004), and references cited therein.

Yet another route to preparing the iminium salts is the direct reaction of certain diamino compounds, such as 1,1-diaminoalkanes, especially substituted diaminoalkanes, and the like with select activating reagents, especially acid chlorides and acid anhydrides. Such processes are also well known. Especially preferred process of this route employ N,N,N',N'-tetraalkyl-1-diaminoaklanes, such as tetramethyldiaminomethane and tetraethyldiaminomethane, as the starting amine.

It is also to be appreciated that many of the suitable iminium salts are available commercially, such as Eschenmoser's chloride and iodide salts which are available from The Aldrich Chemical Co.

Alternatively, and again as noted above, it is to be appreciated that the iminium salts may be formed in-situ, e.g., as an initial step or series of steps in the production of the methylidene malonates. Specifically, rather than using purchased materials or separately preparing, isolating and purifying the iminium salt, the process of preparing the iminium salt is integrated into the overall methylidene malonate production process. Here the iminium salt is formed (by any of the known methods, especially those noted above) and the ethylene precursor added to the iminium salt, or vice-versa. Depending upon the specific process used to produce the iminium salt, it may be desirable, if not necessary, to isolate or consolidate the so formed iminium salt and/or to remove certain components of the reaction mix, especially catalysts in the case of those processes that employ the same, prior to combining the iminium salt with the ethylene precursor.

Most preferably, it is desired to generate the in-situ formed iminium salt using those processes wherein the iminium salt is prepared directly from the reaction of a 1,1-diamine compound and an activator which contributes the appropriate counter ion, either a halide or a non-nucleophilic conjugate base of an acid. Exemplary anion species include, but are not limited to, chloride, bromide, iodide, $AsF_6$, $SbF_6$, $PF_6$, $BF_4$, $CH_3SO_3$, $CF_3SO_3$, benzenesulfonate, para-toluenesulfonate, sulfate, bisulfate, perchlorate, $SbCl_5$, $SbCl_3$, $SnCl_5$, carboxylate, and substituted carboxylate. Generally, the amount of diamine to activator to be used in the reaction process is a molar equivalence, though the amine may be used at a slight excess relative to the malonate starting material. Most preferably, though, the activator is employed at a molar excess as compared with the diamine. For example, the molar ratio (activator:diamine) of 1.0:1 to 10:1, more preferably from 1.2:1 to 5:1 and most preferably from 1.5:1 to 2:1, may be used. These reaction processes occur rapidly and, for the most part, spontaneously: oftentimes requiring cooling to control the exotherm. These reactions are also preferred as the product iminium salt can be used as is and does not require isolation and/or purification.

The preferred iminium salts are the halide salts and the carboxylate salts: though as noted and demonstrated, iminium salts of other anionic species are effective as well. It is also thought that certain benefits may result from the presence of the soft anion (as classified by Pearson's Principles of Hard and Soft Acid Base (HSAB)). In following, although not limited thereto, it is especially preferred that the carboxylate anion is an acetate, a propionate, a pivalate, a stearate, an isobutyrate, or a benzoate; most preferably an acetate.

For purposes of convenience, the present teachings will be discussed in terms of the dialkylmethylideneammonium carboxylate salts, especially the dimethylmethylideneammonium carboxylate salts. However, it is to be appreciated and intended that these teachings are equally applicable to and reflective of the iminium carboxylate salts in general as well as the other iminium salts mentioned above: all of which are suitable for use in the practice of the present process. While not wanting to be bound by theory, it is thought that marked benefit in performance noted with the carboxylate anion, especially in those iminium salts of Formula VI above where $R^4$ and $R^5$ are H and, optionally, though preferably, neither $R^6$ nor $R^7$ contain a tertiary carbon atom bonded to the N atom, occurs as a result of improved solubility.

The dialkylmethylideneammonium carboxylates may be prepared by a variety of methods. For example, they can be prepared by reacting the desired trialkylamine N-oxide with the acid anhydride of the desired carboxylate anion. Alternatively, the desired dialkylamine can be reacted with formaldehyde or a formaldehyde synthon such as paraformaldehyde in the presence of the carboxylic acid. One preferred method is to prepare the dialkylmethylideneammonium carboxylate by an anion exchange reaction with another more common and, preferably, cheaper, dialkylmethylideneammonium salt such as the commercially available dimethylmethylideneammonium halides, especially the iodide (i.e., Eschenmoser's salt).

More preferably, the dialkylmethylideneammonium carboxylate is prepared by the reaction of tetraalkyldiaminomethane with a carboxylic acid anhydride, e.g., dimethylmethylideneammonium carboxylate is prepared by the reaction of tetramethydiaminomethane with a carboxylic acid anhydride. When this method is employed, the molar ratio of tetraalkyldiaminomethane to carboxylic acid anhydride is preferably from 1.0:1 to 10:1, more preferably from 1.2:1 to 5:1 and most preferably from 1.5:1 to 2:1. This reaction is preferably conducted in the presence of a solvent such as acetonitrile or toluene. The process is preferably conducted at and, because the reaction is typically exothermic, maintained at a reaction temperature of between 0° C. to 60° C. Though not critical, it is preferable for reaction control that the carboxylic acid anhydride is added to the tetraalkyldiaminomethane as opposed to latter being added to the former. Furthermore, because the reaction is exothermic, it is preferred to perform the addition gradually or in portions. Exemplary carboxylic acid anhydrides include acetic anhydride, propionic anhydride, isobutyric anhydride, pivalic anhydride, and benzoic anhydride. Preferably, the carboxylic acid anhydride is acetic anhydride because it is readily available and because any unreacted acetic anhydride and any reaction byproducts such as dimethylacetamide are easily removed. Reaction times vary depending upon the reactants and conditions; however, most often the formation of the iminium salt is completed within a few hours, generally within an hour to an hour and a half. Again, shorter or longer times may be necessary to bring the reaction to completion.

As noted above, the dimethylmethylideneammonium carboxylate may be prepared en-mass or acquired and stored for use. However, for cost convenience and overall simplicity and consolidation of process, it is desirable to employ an in-situ formed dimethylmethylideneammonium carboxylate, with or without isolation from its reaction mix. Here, for example, the dimethylmethylideneammonium carboxylate is formed and, without isolation, combined with a diester of malonic acid and allowed to react.

The 1,1-disubstituted ethylene is prepared by combining the iminium salt or the in-situ formed iminium salt reaction product with the ethylene precursor. Although either may be added to the other, it is preferable that the ethylene precursor is added to the iminium salt. The reaction is typically, and preferably, performed at a temperature from 0° C. to 60° C., most typically at room temperature or higher. Higher temperatures can be used and tolerated, but such higher temperatures can result in polymerization or partial polymerization and/or viscosity increase of the formed 1,1-disubstituted ethylene monomer, which results in decreased yields and purity. Similarly, temperatures lower than 0° C. may be used but are not necessary and add to the overall production costs associated with the longer reaction times and the cooling of the reaction system. Furthermore, it is to be appreciated that the specific iminium salt or iminium salt reaction product may also influence the temperature at which the reaction process is carrier out. For example, the presence of excess acid chlorides resulting from the in-situ formation of the halide salts is found to slow the reaction somewhat. Accordingly, elevated temperatures, generally in the range of from 40° C. to 50° C. appear to provide optimal reaction for those salts. Similarly, the reaction appears slower with certain carboxylate salts, again suggesting a desire for elevated temperatures. On the other hand, certain halide salts, such as the Eschenmoser's salts, perform well at room temperature.

The amount of reactants to be employed depends, in part, upon the selected reactants themselves and the impact, if any, of excess on the resultant product or process. Generally speaking, the ratio (on an equivalence basis) of iminium salt to ethylene precursor is from about 1:1 to 10:1, preferably from about 1:1 to 6:1, most preferably, from an economic standpoint, 1:1 to 1:4. Again, it is to be appreciated that certain combinations of reactants will require higher or lower ratio to reach completion, even higher than the stated ranges.

Although not a requirement, it is preferred that the reaction of the reaction of the iminium salt and the ethylene precursor is carried out in the presence of a solvent. Indeed, if the iminium salt is formed in-situ, it is preferable that the iminium salt also be prepared in a solvent, most especially the same solvent as is to be employed for the overall reaction. Preferable solvents have a boiling point at atmospheric pressure of between 40° C. and 150° C. Solvents with lower boiling points can cause difficulty and reaction instability because the reaction is exothermic, or in some cases too slow and require heating. Solvents with higher boiling points can be difficult to remove in subsequent purification steps. Furthermore, as noted above, where the iminium salt is formed in-situ, it is preferred that the same solvent is used for both its preparation as well as in the reaction with the ethylene precursor.

The solvents employed may be polar or nonpolar solvents. Exemplary polar solvents include, but are not limited to, DMF, THF, acetonitrile, DMSO, IPA, ethanol and the like. Exemplary nonpolar solvents include, but are not limited to, toluene, benzene, diethylether, hexane, cyclohexane and carbontetrachloride. Polar solvents appear to be optimal for reaction performance in preparing the methylidene malonate; however, pose difficulties in the subsequent work-up to purify and isolate the methylidene malonate. In this respect, it is more difficult to remove the polar by-products from the reaction. On the other hand, nonpolar solvents do not provide optimum reaction performance, but make work-up and isolation and purification much simpler and more efficient. It is also to be appreciated that one can conduct the reaction in a polar solvent and then switch the solvent to a nonpolar solvent before performing any steps to isolate and/or purify or treat the methylidene malonate monomer. Furthermore, it is preferred to use the lower boiling point solvents since the higher temperatures needed for distillation of reaction mixes with higher boiling point solvents may lead to polymerization and/or degradation of the monomer.

Generally speaking the amount of solvent to be used is from about 5× to about 30×, preferably about 10× to about 25×, most preferably, on an economic and environmental basis, about 15× to about 20×, the amount of malonic acid ester, on a volumetric basis.

Reaction times for the production of the methylidene malonates will also vary depending upon the reactants, reaction temperature, and the choice of solvent. Reaction times range from under an hour to many hours, indeed 20 or more hours may be necessary to attain complete reaction. Typically, a reaction time of an hour or so up to six hours is suitable and sufficient.

Likewise, though not a requirement, it is preferred that the reaction of the ethylene precursor and the iminium salt occurs in the presence of an acid or its anhydride, preferably an acid having a pKa less than 6.0, more preferably less than 5.0. This is especially so for the reaction involving carboxylate ester ethylene precursors, most especially when the ethylene precursor is a malonic acid ester or diester. The presence of the acid or anhydride is believed to stabilize the 1,1-disubstituted ethylene monomer product from polymerization. Suitable acids and anhydrides for preventing the polymerization of 1,1-disubstituted ethylene monomers are well known and discussed at length in Malofsky et. al. (US WO 2010/129068), which is hereby incorporated herein by reference in its entirety. Exemplary acids and anhydrides include, but are not limited to, acetic acid, acetic anhydride, trifluoroacetic acid, alkyl sulfonic acids such as methanesulfonic acid or trifluoromethanesulfonic acid, arylsulfonic acids such as toluenesulfonic acid, and sulfuric acid. When used, the amount of acid to be added to the reaction mix is preferably from about 100 to about 20,000 ppm, preferably from about 300 to about 10,000 ppm, most preferably from about 2000 to about 5000 ppm based on the amount of the diester of malonic acid. Optimum levels of acid to be added to a given reaction mix can be determined by simple experimentation.

Additional stabilization may be imparted to the reaction mix, especially following or towards the end of the reaction, by the addition of one or more free radical polymerization inhibitors. The free radical stabilizer or polymerization inhibitor, as they are more commonly referred, may be added alone or in combination with the acid stabilizer, or any anionic polymerization inhibitor, again as mentioned in Malofsky et. al. Suitable free radical inhibitors include, but are not limited to, the hydroquinones and various hindered phenols, especially para-hydroquinone monomethyl ether, catechol, pyrogallol, benzoquinones, 2-hydroxy benzoquinones, t-butyl catechol, butylated hydroxy anisole (BHA), butylated hydroxy toluene (BHT), t-butyl hydroquinones, 2,2"-methylene-bis(6-tert-butyl-4-methylphenol), and mixtures thereof. The amount of free radical inhibitor to be added to the system should generally be from about 100 to about 20,000 ppm, preferably from about 300 to about 10,000 ppm, most preferably from about 2000 to about 5000 ppm based on the amount of the diester of malonic acid. As with the acid stabilizer, the optimal amount of free radical polymerization inhibitor to be used can be determined by simple experimentation.

The 1,1-disubstituted ethylenes formed by the reaction of the ethylene precursors and the iminium salts may be used as-is, but are preferably subjected to various separation, isolation and/or purification steps, all of which are well known in the art. Where the reaction is conducted in a solvent wherein the reaction product is highly soluble therein, it is preferable to replace the solvent with another solvent having no or less solubility properties for the formed 1,1-disubstituted ethylene monomer. Again, insofar as isolation and purification of the monomer is concerned, any of the known methods for purification of like organic molecules can be employed; however, purification is preferably achieved by distillation, most preferably under reduced pressure as this allows for lower distillation temperatures. Like the concern with higher reaction temperatures, higher distillation temperatures increase the potential for polymerization or partial polymerization of the methylidene malonate, thereby decreasing the yield.

As noted, it may be desirable to isolate the 1,1-disubstituted ethylene monomer material from the reaction mix prior to purification, and especially prior to use. Isolation helps remove unreacted reactants and reaction byproducts. Isolation can be performed by any of the methods known in the art for such purpose. For example, isolation may be conducted as a low temperature distillation under reduced pressure. Alternatively, isolation may be achieved by solvent washing and separation, exemplary solvents include water.

Yet another alternative is the treatment of the crude reaction product with a solid adsorbent such as alumina to remove unreacted reactants and reaction byproducts. Preferably, isolation is achieved by a combination of these techniques.

Following the teachings of Malofsky et. al., the isolation and/or purification steps are preferably conducted in the presence of one or more stabilizers/polymerization inhibitors, especially anionic polymerization inhibitors, most especially acid polymerization inhibitors, and/or free radical polymerization inhibitors, most preferably both. Suitable polymerization inhibitors are discussed above and, in more detail, in Malofsky et. al. which, again, is hereby incorporated hereby by reference in its entirety. Preferably the anionic stabilizer/polymerization inhibitor is an acid stabilizer, most preferably an acid having a pKa less than 2.0. Exemplary acids include trifluoroacetic acid, alkyl sulfonic acids such as methanesulfonic acid or trifluoromethanesulfonic acid, arylsulfonic acids such as toluenesulfonic acid, and sulfuric acid.

Although the stabilizers may be used in any isolation process, they are most preferably used in those isolation processes that involve elevating or elevated temperatures or any other conditions that are know to promote, accelerate or initiate polymerization of 1,1-disubstituted ethylene monomer. In any event, stabilizers should, and preferably are, employed in the purification steps, with addition thereof to the distillation pot as well as the collection or receiver vessel. Stabilizers are also to be added to the final collected materials to inhibit polymerization during subsequent storage. Generally speaking the amount of stabilizer (anionic polymerization inhibitor, free radical polymerization inhibitor or both) to be added to the 1,1-disubstituted ethylene monomer reaction product, crude reaction product and/or isolated product should be from about 100 to about 20,000 ppm, preferably from about 300 to about 10,000 ppm, most preferably from about 2000 to about 5000 ppm based on the amount of the 1,1-disubstituted ethylene monomer. Preferred or optimal stabilizers or combinations of stabilizers as well as the amount thereof to use can be determined by simple experimentation Having disclosed the general aspects and reagents to be employed in the presently taught and claimed process, attention now is directed to the specific aspects, each of which are new and/or improvements over the state of the art.

According to a one aspect of the present teachings, those processes in which an ethylene precursor is reacted with an iminium salt to form a 1,1-disubstituted ethylenes is improved by the addition of an acid halide, especially an acid chloride, and/or an acid anhydride to the reaction mix and/or product. The addition of the acid halide and/or acid anhydride has been found to reduce the formation of dimer. In this regard, it is believed that the reaction process generates amines, especially secondary amines, like diethylamine and their salts, which catalyze or promote dimer formation. The addition of the acid halide and/or acid anhydride are believed to scavenge these amines, thereby preventing the formation of the dimers. The acid halide and/or acid anhydride may be added at any time, though it is especially beneficial to add it to the reaction mix before or during the reaction. The amount of acid halide and/or acid anhydride to be added is not so critical and can be found by simple experimentation for a particular reaction system. Oftentimes an amount of up to a molar equivalent based on the amount of iminium salt present is sufficient: though larger amounts could be used. Generally lesser amounts, e.g., 0.2 to 0.5 eq. will suffice.

Alternatively, one may achieve the foregoing benefit by generating the iminium salt is-situ and using an excess of an acid halide and/or acid anhydride in the iminium salt formation. By this method, in addition to forming the desired iminium halide or iminium carboxylate one also adds to the reaction mix sufficient acid halide and/or acid anhydride to scavenge the amines. In this instance, the molar ratio of acid halide or acid anhydride is generally higher than or at the higher end of the ratio of activator to diamine discussed above. Here, it is preferred that the molar ratio is from 1.2:1 to 10:1, preferably from 1.5:1 to 7:1, and most preferably from 1.5:1 to 5:1, may be used.

Acid halides are well known and widely available. These generally correspond to the formulae $R^9C(O)X$ and $R^9SO_2X$ where $R^9$ is an aliphatic or aromatic hydrocarbon or substituted hydrocarbon, especially a $C_1$ to $C_{18}$, preferably a $C_1$ to $C_{12}$, more preferably a $C_1$ to $C_6$, hydrocarbon or substituted hydrocarbon, and X is fluorine, chlorine, bromine or iodine. Preferred acid halides are those wherein R9 is a $C_1$ to $C_6$ hydrocarbon and X is chlorine. Especially preferred are the acid chlorides, i.e., those compounds having the foregoing formula wherein X is chlorine, including the acyl chlorides, the aroyl chlorides and the sulfonyl chlorides. Exemplary acid chlorides include acetyl chloride, propionyl chloride, isobutyryl chloride, trimethylacetyl chloride, benzoyl chloride, and chloroacetylchloride Similarly, acid anhydrides are well known and widely available. These are organic compounds that has two acyl groups bound to the same oxygen atom. Most commonly, the acyl groups are derived from the same carboxylic acid and correspond to the general formula $(R^9C(O))_2O$, wherein $R^9$ is as defined above. Exemplary acid anhydrides include formic acid anhydride, acetic anhydride, propionic anhydride, butyric anhydride, valeric anhydride, caprilic anhydride, trifluoroacetate, isobutyric anhydride, trimethylacetic anhydride, trifluoroacetic anhydride, and sulfonic acid anhydride.

Another aspect of the present teachings pertains to the select use of iminium carboxylates, either preformed or formed in-situ, in the processes for the production of the 1,1-disubstituted ethylenes. Specifically, it has been found that the select use of the iminium carboxylates allows one to use non-polar solvents as the solvent for the iminium preparation and/or the reaction of the iminium salt and the ethylene precursor. Although non-polar solvents do not, in many instances, provide for the optimal conversion of ethylene precursor to 1,1-disubstituted ethylene, they do allow for more efficient and effective separation, isolation and/or purification of the formed 1,1-disubstituted ethylene monomer. This benefit manifest in several respect including better yields as extraction of the 1,1-disubstituted monomer is easier and more complete than from polar solvents, particularly those monomers that are highly soluble in polar solvents.

Another advantage of the use of iminium carboxylates is the finding that, in many, if not most instances, the reaction to form the 1,1-disubstituted ethylenes can be conducted at room temperature or slightly elevated temperatures. This compares with many of the acid chlorides which have a tendency to slow the reaction down, oftentimes necessitating elevated temperature reaction conditions, generally 30° C. to 65° C. and higher.

Although it is possible to perform a solvent swap, wherein a non-polar solvent is substituted for a polar solvent following the reaction process, such processes are time consuming, require the use of additional materials, including expensive solvents like acetonitrile. Thus, it is especially beneficial to be able to use non-polar solvents from the outset: a practice that is enabled by the select use of iminium carboxylates.

Yet another feature of the present teachings is the finding that one can improve yields and stability by treating the 1,1-disubstituted ethylene reaction product with a solid phase material known to adsorb or absorb polar materials in the presence of a non-polar solvent following completion of the reaction. If the reaction process to form the 1,1-disubstituted ethylene is conducted in the presence of a polar solvent, one must first remove and replace the polar solvent with a non-polar solvent. Treatment with the solid phase material is performed following the reaction itself and prior to any further efforts to isolate, separate and/or purify the 1,1-disubstituted ethylene monomer. The treatment is continued until most, if not substantially all, of the polar impurities are absorbed or adsorbed, after which the reaction product is then isolated/separated from the solid phase material, e.g., by filtration, centrifugation, decanting, distillation, thin film evaporation, etc. Suitable solid phase materials include ion-exchange resins, molecular sieves, zeolites, alumina, and the like, provided that the same are acidic to neutral pH, preferably acidic. Acidic materials are needed to prevent or guard against polymerization of the monomer since many of the 1,1-disubstituted ethylene monomers are base catalyzed or activated.

This treatment process will typically employ a large amount of the solid phase material, generally up to 100 wt % or more based on the monomer to be treated. Typically, the amount is from about 30 wt % to about 80 wt %, preferably from about 40 wt % to about 70 wt %. The high amount is to enable faster scavenging of the impurities while minimizing exposure, particularly since the solid phase materials oftentimes adsorb or absorb TFA and other key stabilizers. Again, because of the high reactivity of the 1,1-disubstituted ethylenes, especially the cyanoacrylate monomer and the methylidene malonate monomers, it is best to complete the treatment as quickly as possible, removing the solid phase material and them up-stabilizing the monomer as necessary. The specific amount and time of the solid phase material treatment will vary depending upon the solid phase material itself, the reaction product being treated, the temperature, etc.

Finally, another improvement to the method of producing 1,1-disubstituted ethylenes using iminium salts comprises treating the isolated and/or purified 1,1-disubstituted ethylene with a slightly acidic to mildly basic alumina and thereafter separating the alumina from the treated 1,1-disubstituted ethylene. This method is disclosed at length in co-pending, co-filed US patent application entitled "Improved 1,1-disubstituted Ethylene Process", Mc Conville et. al. and U.S. Provisional Patent Application No. 61/591,882, filed 28 Jan. 2012, the contents of which are hereby incorporated herein in their entirety by reference.

Generally speaking, this method entails treating the isolated and/or purified 1,1-disubstituted ethylene with an alumina having a pH, as measured in neutral water, of generally from about 5.0 to about 8.5, preferably from about 5.5 to about 8.5, more preferably from about 6.0 to about 8.0, most preferably from about 6.5 to about 7.5. Typically, the alumina treatment is conducted at from about 0° C. to about 150° C., preferably from about 20° C. to 70° C., for from about 5 minutes to about 20 hours, preferably from about 10 minutes to 5 hours. The quantity of alumina employed depends upon many factors, including the method employed. Generally speaking, especially in batch processing, the amount of alumina is from about 0.5 to about 20 weight percent, preferably from about 2 to about 10 weight percent, based on the weight of the monomer. In the case of continuous processing, the amount of alumina is determined by the retention time in the treatment container or column. Specifically, one must ensure proper retention time in order to ensure sufficient treatment or one may circulate the monomer through the column until the desired effect is realized.

By implementing the improved processes as set forth herein, one realizes more consistent and improved yields. For example, one may attain crude yields in excess of 50%, preferably in excess of 60%, more preferably in excess of 80%, most preferably in excess of 90%, with purities of, generally, 60% or more, preferably 70% or more, more preferably 80% or more, most preferably 90% or more. Owing to the initial high purity of the crude products, subsequent purification allows for the even higher purity materials with a modest to minimal effect on yield. For example, purified yields in excess of 25%, preferably in excess of 30% with purities of, generally, 90% or more, preferably 95% or more, more preferably 98% and even 99% or more are readily attainable.

The 1,1-disubstituted ethylenes resulting from the present teachings are well known, though not all have yet made it to commercial success. These monomers may be employed in a number of organic syntheses and polymer chemistry applications. In particular, they are especially useful in the preparation of various adhesive and sealant applications including industrial, commercial and consumer adhesive and sealant applications as well as in medical adhesives, most especially skin bonding applications for human and animal skin bonding. In light of the benefit of the present invention, it is believed that these compositions are now commercially viable as cost effective and stable formulations can now be made.

EXAMPLES

Having described the invention in general terms, Applicants now turn to the following examples in which specific combinations of reactants, solvents and reaction times were evaluated. These examples are presented as demonstrating the surprising attributes of the improved processes of the present. These examples are merely illustrative of the invention and are not to be deemed limiting thereof. Those skilled in the art will recognize many variations that are within the spirit of the invention and scope of the claims.

Iminium Salts

A plurality of preformed and in-situ formed iminium salts were employed. The general structures of these salts were as follows:

Halogen Based Salts:

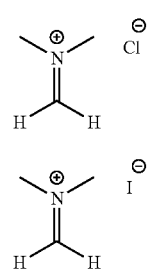

Carboxylate Salts:

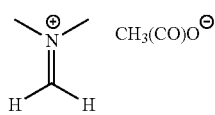

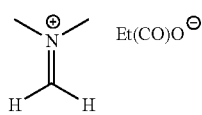

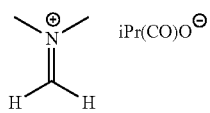

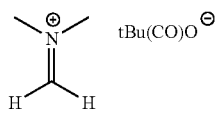

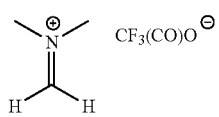

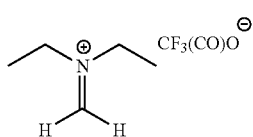

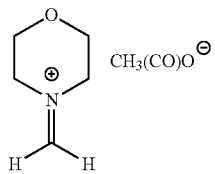

Sulfonate Salts:

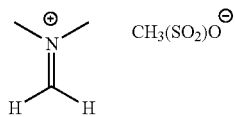

Monomer

Similarly, three different monomer substrates containing a methylene linkage having attached thereto at least one electron withdrawing group were employed to further demonstrate the breadth of the present teachings as follows:

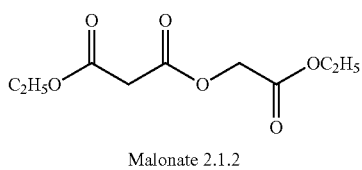

Malonate 2.1.2

Malonate 2.2

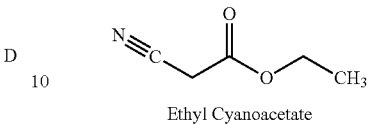

Ethyl Cyanoacetate

DMDEE Test

In order to assess cure performance of the 1,1-disubstituted ethylene monomers, a standardized test based on dimorpholinodiethyl ether ("DMDEE") as a cure initiator/activator was developed. This standardized test allowed direct comparison from treated and untreated 1,1-disubstituted ethylene monomers as well as between different types of treatments and variations of the same types of treatments. Specifically, the cure characteristics of 1,1-disubstituted ethylene monomers were assess by inducing the polymerization of the monomers in the presence of DMDEE as follows:

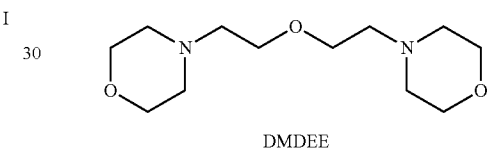

DMDEE

To a tared 4 mL glass vial equipped with a magnetic stir bar, 55 microliters of a 10% by weight solution of DMDEE in isopropanol is added. The vial is reweighed to determine the weight of solution added and monomer is added to the DMDEE solution while stirring to give 1 mL monomer per 42.5 mg DMDEE solution. Stirring is continued for one minute. The stir bar is removed and replaced with a thermocouple. Temperature is plotted versus time. The polymerization induction time is taken as the time in which the rise in temperature between two successive data points (three point running average) first exceeds 0.5° C. A short induction time is indicative of a monomer that is suitably active for commercial use, i.e., will polymerize in a reasonable period of time. A long induction time is indicative of a monomer that, most likely due to the presence of impurities which inhibit polymerization, that is unsuitable for commercial use owing to the lack of polymerization or a cure speed that is too slow to be of commercial utility.

Example 1

Eschenmoser's Iodide Salt (EIS)

6 eq. of EIS (Iminium B) and 0.1 eq. of TFA, were added to Malonate 2.1.2 in 20 volumes of 19:1 DMF:IPA solvent. The mixture was stirred for 12-24 hours at room temperature and produced an in-solution yield of ~30% of Methylidene Malonate 2.1.2. Analysis of the reaction product showed considerable dimer formation as well.

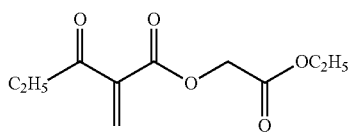

Methylidene Malonate 2.1.2

Example 2

Reverse Addition

Malonate 2.1.2 dissolved in DMF was slowly added to 6 eq. of EIS (Iminium B) over a period of 2 hours with stirring at room temperature. A measurement was taken after 22 hours and it was found that an in-solution yield of Methylidene Malonate 2.1.2 of 45% had been attained. A further 3 eq. of EIS dissolved in DMF was added after 22 hours and the reaction continued at room temperature for an additional 18 hours. The reaction product then showed an in-solution yield of 47%. Analysis of the reaction product continued to showed considerable dimer formation as well.

Example 3

Acid Chloride Addition

Malonate 2.1.2 dissolved in DMF was slowly added to 3 eq. of EIS (Iminium B) over a period of 2 hours with stirring. A measurement was taken after 4 hours and it was found that an in-solution yield of Methylidene Malonate 2.1.2 of 26% had been attained. 0.25 eq. of acetyl chloride was then added to the reaction mix and the reaction continued for an additional 16 hours. The reaction product then showed an in-solution yield of 47%; however, the level of dimer was markedly reduced after the addition of the acetyl chloride, indeed, even lower than was present before the addition of the acetyl chloride. It is theorized that the acid chloride prevents the dimer formation and may actually reverse its formation, possibly via a retro Michael addition.

Example 4

Acid Chloride Addition and Higher Temperatures

Having noted that the addition of the acetyl chloride (AcCl) appeared to slow the reaction process at room temperature, another experiment was conducted to consider the impact of higher temperature in combination with the acetyl chloride addition. To correlate the impact of the acetyl chloride and temperature on the reaction and reaction products, both percent conversion of the Malonate 2.1.2 and the percent of Methylidene Malonate 2.1.2 in the reaction products were assessed: dimer typically accounting for sizeable portion of the reaction product. The specific steps and results are presented in Table 1.

TABLE 1

| Time (hr) | Comment | Conversion (%) | Percentage of Monomer in Products (%) |
|---|---|---|---|
| 1 | Malonate was added over 1 hr to 3 eq EIS | 46 | 55 |
| 3 | Added 0.25 eq of AcCl after 1 hr | 33 | 73 |

TABLE 1-continued

| Time (hr) | Comment | Conversion (%) | Percentage of Monomer in Products (%) |
|---|---|---|---|
| 6 | Added additional 3 eq of EIS after 3 hrs | 38 | 75 |
| 7 | Started heating to 40° C. | 57 | 73 |
| 21 | After 14 hr at 40° C. | 62 | 65 |
| 23 | Added additional 0.25 eq AcCl | 57 | 72 |
| 25 | Added additional 3 eq EIS | 61 | 72 |
| 41 | Heated to 50° C. | 85 | 57 |

The results shown in Table 1 clearly demonstrate the marked improvement in yield of the desired Methylidene Malonate 2.1.2 as a result of the addition of the acetyl chloride. Higher temperature appeared to accelerate the conversion; however, elevating the temperature too high with the further addition of EIS led to a loss in the benefit of the acetyl chloride. Presumably, the added EIS led to additional dimer formation and/or degradation of the Methylidene Malonate 2.1.2. Additionally, it is to be recognized that acetyl chloride boils at 52-55° C. and, thus, higher temperatures may lead to a loss in acetyl chloride itself from the reaction pot.

Example 5

In-Situ Eschenmoser's Chloride Salt (ECS)

A series of experiments were run to assess both the ability to use an in-situ formed Eschenmoser's salt, in this case Eschenmoser's chloride salt (ECS-Iminium A), in the production of 1,1-disubstituted ethylenes as well as the impact of varying the mole ratio of the salt forming ingredients on the same. In this specific set of experiments the ECS was formed by the reaction of varying amounts of acetyl chloride and 6 Eq. of tetramethyldiaminomethane (TMDAM) in DMF at 0° C. Following the formation of the ECS, Malonate 2.1.2 dissolved in DMF was slowly added to the reaction product of the ECS formation and the mixture heated to 60° C. The specific experiments and the results attained thereby are presented in Table 2.

TABLE 2

| Run | Eq of AcCl | Reaction Time (hr) | Conversion (%) | Percentage of Monomer in Products (%) |
|---|---|---|---|---|
| 1 | 6.5 | 16 | 98 | 62 |
| 2 | 6.5 | 21 | 99 | 45 |
| 3 | 7.5 | 21 | 99 | 69* |
| 4 | 9 | 25 | 59 | 70 |
| 5 | 12 | 25 | 22 | 55 |

*this corresponds to an in-solution yield of Methylidene Malonate 2.1.2 of 68% (% conversion times % Monomer in Products)

Example 6

Use of Acetonitrile as Solvent

Given the relatively high boiling point of DMF, acetonitrile was evaluated as an alternate polar solvent, as well as to assess whether other polar solvents were suitable. In this experiment 300 ml of acetonitrile was added to a three neck round bottom flash containing 6 eq. TMDAM (56.2 g) and the mixture cooled in an ice bath to 2-3° C. 7.5 eq. acetyl chloride (48.8 ml) was then added slowly at a rate whereby the temperature of the reaction mix was maintained 20° C. After the addition was completed, the mixture was removed from the ice bath and allowed to come to room temperature while stirring (~1 hour). Once at room temperature, 1 eq. of Malonate 2.1.2 monomer (20 g) dissolved in acetonitrile (5 ml) was slowly added. Once the addition was completed, the mixture was stirred for one hour at room temperature and then the mixture heated to 60° C. and stirred for an additional 24 hours. This produced a reaction product with a 97% conversion and an in-solution yield of 80%, as determined by GC.

Once the reaction was complete, the crude reaction mix was cooled to 30° C. and 400 ml of MTBE added to precipitate/crash out the amine salts. The solids were removed by filtration (at continued cold temperature to avoid the salts from going back into solution/melting) and the remaining filtrate was found to have an in-solution yield of 73%.

Example 7

Use of Different Acid Chlorides

A further series of experiments were conducted to assess the suitability of various acid chlorides in the iminium process. The same process as employed in Example 6 was employed here as well with the exception of the acid chloride and the mole ratios of the same and the TMDAM. The specific experiments and the results attained thereby are presented in Table 3.

TABLE 3

| Run | TMDAM (eq) | Acid Chloride (eq) | Time (hr) | Conversion (%) | In-Solution Yield (%) |
|---|---|---|---|---|---|
| 1 | 6 | propionyl chloride (7.5) | 18 | 98 | 85 |
| 2 | 3 | propionyl chloride (4.5) | 20 | >99 | 91 |
| 3 | 2 | propionyl chloride (3.5) | 20 | 90.5 | 82 |
| 4 | 3 | isobutyryl chloride (4.5) | 20 | 98.6 | 80 |
| 5 | 3 | 3-methylbutanoyl chloride (4.5) | 20 | 97.5 | 89.9 |
| 6 | 3 | pivaloyl chloride (4.5) | 20 | 99 | 94.4 |
| 7 | 2 | pivaloyl chloride (3.5) | 20 | 78.5 | — |

Substituting the propionyl chloride (Run 1) for the acetyl chloride (Example 6) while keeping everything else the same presented an immediate jump in yield of ~5%. The yield jumped even higher when the amount of amine was reduced to 3 eq. and the amount of chloride reduced to 4.5 eq.

Example 8

Procedure Using Acetonitrile with Work Up to Remove Ammonium Salts

In this experiment 15 ml of acetonitrile was added to a three neck round bottom flask containing 3 eq. TMDAM (1.4 g) and the mixture cooled in an ice bath to 2-3° C. 4.5 eq. propionyl chloride (1.8 ml) was then added slowly at a rate whereby the temperature of the reaction mix was maintained below 20° C. After the addition was completed, the mixture was removed from the ice bath and allowed to come to room temperature while stirring (~1 hour). Once at room temperature, 1 eq. of Malonate 2.1.2 monomer (1 g) dissolved in acetonitrile (5 ml) was slowly added. Once the addition was completed, the mixture was stirred for one hour at room temperature and then the mixture heated to 60° C. and stirred for an additional 10 hours. This produced a reaction product with an in-solution yield of 91%, as determined by GC.

Once the reaction was complete, the crude reaction mix was concentrated to remove most of the acetonitrile. The remaining reaction product appeared as a viscous oil to which was added toluene and the mixture distilled twice. The mixture was then dissolved in 10 volumes of toluene and an equal amount of MTBE. The resultant slurry was then filtered to remove the solids leaving a solution of the methylidene malonate 2.1.2 monomer at an in-solutions yield of 80%.

Example 9

Polar and Nonpolar Solvents with Acid Anhydride to Prepare Iminium Salts

A series of experiments were run with polar (acetonitrile) and nonpolar (toluene) solvents. The general procedure for both types of solvents is pretty much the same and begins with the addition of 15 volumes of the selected solvent to 2 eq. of the diamine in a round bottom flask kept under nitrogen atmosphere. The reaction mixture is then cooled to 0-5° C. using an ice bath and 3.5 eq. of the acid anhydride is added to the chilled reaction mix at a rate whereby the internal temperature never exceeds 10° C. After the addition is complete, the mixture is removed from the ice bath and allowed to warm to room temperature, generally over a period of 1-1.5 hours. A solution of the malonate to be converted and 0.1 eq. sulfuric acid or trifluoroacetic avid (TFA) in 5 volumes of the same solvent is then slowly added to the reaction mixture at a rate such that the internal temperature never exceeds 25° C. Thereafter the processes differ with that process employing the polar solvent continuing to react at room temperature for a few hours, typically less than 6. That process using the non-polar solvent, on the other hand, involved heating the reaction mix to 40° C. and allowing the reaction to continue to completion, generally 15-20 hours.

Table 4 presents the results attained with a number of different acid anhydride derived iminium salts/reaction products in accordance with the general procedure of the preceding paragraph.

TABLE 4

| Iminium salt | Conditions (salt introduction) | Solvent | In-solution yield (%) |
|---|---|---|---|
| C | In-situ synthesis from acetic anhydride | Acetonitrile | 68 |
| E | In-situ synthesis from isobutyric anhydride | Toluene | 27 |
| F | In-situ synthesis from trimethylacetic anhydrid | Toluene | Not measured- (89% conversion) |

Example 10

Use of Iminium I for Methylidene Malonate 2.1.2 Preparation

Iminium I was generated from N,N,N',N'-tetraethyl-diaminomethane in a manner analogous to the in situ generation of Iminium C (see Example 9). Thus, 2.90 g of N,N,N',N'-tetraethyldiaminomethane was dissolved in acetonitrile (30 mL) and the solution was cooled to 0-5° C. in an ice-water bath. Acetic anhydride (3.28 g) was added, causing the temperature to rise to ~10° C. The ice bath was removed and the mixture was stirred for ~1 hr. The mixture was placed back in an ice-water bath and cooled back to ~15° C. A solution of Malonate 2.1.2 (2.00 g) and trifluoroacetic acid ((0.11 g) in acetonitrile (10 mL) was then added and the ice-water bath was again removed. After warming to 20-25° C., the mixture was stirred for an additional 2 hr, at which point the in-solution yield was measured at 67%.

Example 11

Use of Iminium J for Methylidene Malonate 2.1.2 Preparation

Iminium J was generated from N,N',-dimorpholinomethane in a manner analogous to the in situ generation of Iminium I (see Example 10). Thus, 3.42 g of N,N'-dimorpholinomethane was dissolved in acetonitrile (30 mL) and the solution was cooled to 0-5° C. in an ice-water bath. Acetic anhydride (3.28 g) was added, causing the temperature to rise to ~10° C. The ice bath was removed and the mixture was stirred for ~1 hr. The mixture was placed back in an ice-water bath and cooled back to ~15° C. A solution of Malonate 2.1.2 (2.00 g) and trifluoroacetic acid ((0.11 g) in acetonitrile (10 mL) was then added and the ice-water bath was again removed. After warming to 20-25° C., the mixture was stirred for an additional 2 hr, at which point the in-solution yield was measured at 75%.

Example 12

Scavenger 320 ml of toluene and 1.1 eq. of TMDAM (13.8 ml) was added to a round bottom flask and kept under nitrogen atmosphere. The reaction mixture was then cooled to 0-5° C. using an ice bath and 2.5 eq. of the acetic anhydride (21.7 ml) was added to the chilled reaction mix at a rate whereby the internal temperature never exceeds 10° C. After the addition was complete, the mixture was removed from the ice bath and allowed to warm to room temperature, generally over a period of 1-1.5 hours. A solution of 1 eq. Malonate 2.1.2 (20 g) and 0.1 eq. sulfuric acid dissolved in toluene (80 ml) was then slowly added to the reaction mixture at a rate such that the internal temperature never exceeds 25° C. (10-15 minutes). The reaction was sluggish at room temperature but improved upon heating. On heating at 40° C., a conversion of ~90% was attained after 20 hours, with an in-solution yield of ~62%.

The reaction mixture was cooled to room temperature and 0.1 eq. concentrated sulfuric acid (0.49 ml) added. 13.26 g acidic, activated alumina (66 wt. %) was then added to the reaction mix and stirred at room temperature for 1.5 hours to remove impurities, particularly, it is believed amine salt impurities. GC analysis before and after the acidic alumina treatment confirmed the removal of impurities. The so formed slurry is filtered and the filtrate up-stabilized with 0.05 eq. conc. sulfuric acid (0.295 µl) before being subjected to a rotary evaporator at 20-22° C. under high vacuum to remove toluene. The crude product was then transferred to a distillation pot and up-stabilized with an additional 0.05 eq. sulfuric acid before commencing distillation. The pot was heated to 50° C. and maintained at that temperature under vacuum for at least 30-45 minutes. It is believed that dimethylacetamide is produced as a byproduct and this step will ensure its removal to avoid decomposition of the product. On further heating, Methylidene Malonate 2.1.2 was recovered at a pot temperature of 156° C., a head temperature of 125° C. and a vacuum of 0.25 mmHg in a collection vessel containing 0.05 eq. sulfuric acid. The isolated monomer product was 89.5% pure by GC analysis. A second distillation of the isolated product yielded 6 g (28%) of 98.8% pure Methylidene Malonate 2.1.2 monomer.

Portions of the isolated monomer were treated with neutral alumina (WN-3, 6.5 pH) at 40° C. for 20 minutes and induction times tested for the treated and untreated monomer. The alumina treatment resulted in the DMDEE induction time dropping from 134 minutes for the untreated monomer to 37 minutes and less than 5 minutes after treatment with at 6.7 wt % and 20 wt %, respectively.

Example 13

Scavengers 2

Similar experiments were conducted using other scavengers including A molecular sieves and ion-exchange resins such as Dowlex Amberlyst 15. Results indicated that these too removed some of the impurities, however the acidic alumina appeared to be more effective.

Example 14

Malonate 2.2

Tetramethyldiaminomethane (TMDAM, 1.1 eq.) and acetonitrile (15 volumes) were added to a round bottom flask and kept under nitrogen. The reaction mixture was cooled to 0-5° C. using an ice-bath. Acetic anhydride (2.5 eq.) was added to the chilled reaction mixture at a rate such that the internal temperature never exceeded 10° C. After the addition was complete, the ice-bath was removed and the reaction was allowed to warm up to 20° C. over a period of 1-1.5 hours. A solution of Malonate 2.2 (1 eq) and acid (trifluoroacetic acid) (0.1 eq.) was prepared in acetonitrile (5 volumes) and was added slowly at a rate such that the internal temperature never exceeded 25° C. (time of addition=10-15 minutes). The reaction was complete in two hours at room temperature and achieve an in-solution conversion of 76%.

Example 15

Cyanoacrylate

Tetramethyldiaminomethane (TMDAM, 1.1 eq.) and acetonitrile (15 volumes) were added to a round bottom flask and kept under nitrogen. The reaction mixture was cooled to 0-5° C. using an ice-bath. Acetic anhydride (2.5 eq.) was added to the chilled reaction mixture at a rate such that the internal temperature never exceeded 10° C. After the addition was complete, the ice-bath was removed and the reaction was allowed to warm up to 20° C. over a period of 1-1.5 hours. A solution of Ethyl Cyanoacetate (1 eq) and acid (sulfuric acid or trifluoroacetic acid) (0.1 eq.) was prepared in acetonitrile (5 volumes) and was added slowly at a rate such that the internal temperature never exceeded 25° C. (time of addition=10-15 minutes). The reaction was complete in two hours at room temperature and achieve an in-solution conversion of 99%.

Although the present invention has been described with respect to aforementioned specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles embraced or embodied thereby.

We claim:
1. A method of producing methylidene malonates and cyanoacrylates which method comprises reacting
   (A) (i) a malonic acid ester corresponding to the formula VI:

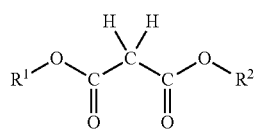

wherein $R^1$ is hydrogen (H) and $R^2$ is a $C_1$ to $C_{18}$ hydrocarbon or heterohydrocarbon group, the latter having one or more nitrogen, halogen, or oxygen atoms or both $R^1$ and $R^2$ are independently a $C_1$ to $C_{18}$ hydrocarbon or heterohydrocarbon group; the latter having one or more nitrogen, halogen, or oxygen atoms or
   (ii) a cyanoacetate corresponding to the formula V:

$CH_2(CN)CO_2R^2$ wherein $R^2$ is a $C_1$ to $C_{18}$ hydrocarbon or heterohydrocarbon group, the latter having one or more nitrogen, halogen, or oxygen atoms, respectively, with
   (B) an iminium salt corresponding to the formula

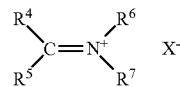

wherein $R^4$ and $R^5$ are both hydrogen (H) and $R^6$ and $R^7$ are each independently a $C_1$ to $C_{10}$ hydrocarbon or substituted hydrocarbon or together form a bridge whereby the nitrogen atom, $R^6$ and $R^7$ together form a ring structure; provided that neither of $R^6$ and $R^7$ is a hydrocarbon moiety comprising a tertiary carbon attached to the N atom, and X is a halogen, a carboxylate or a sultanate anion,
   in the presence of
   (C) from 0.2 to 1.0 equivalents based on the iminium salt (B) of (i) an acid halide of the formula $R^9C(O)X$ or $R^9SO_2X$, (ii) an acid anhydride of the formula $R^9C(O)_2O$ or (iii) both (i) and (ii), wherein $R^9$ is an aliphatic or aromatic $C_1$ to $C_{18}$ hydrocarbon or substituted hydrocarbon and X is fluorine, chlorine, bromine or iodine.

2. The method of claim 1 wherein in the iminium salt (B) $R^6$ and $R^7$ are each independently a $C_1$ to $C_6$ alkyl or alkenyl group and X is a halogen or carboxylate anion.

3. The method of claim 1 wherein compound (A) is a malonic acid ester (i) of formula VI and one or both of $R^1$ and $R^2$ are independently, a $C_1$ to $C_{10}$ linear or branched alkyl group, a $C_3$ to $C_6$ alicyclic group, a $C_2$ to $C_6$ alkenyl group, or a $C_2$ to $C_6$ alkynyl group, which group(s) may be substituted with or contain an ether, epoxide: halo, ester, cyano, aldehyde, keto or aryl group.

4. The method of claim 3 wherein at least one of $R^1$ and $R^2$ is of the formula:

—$(CH_2)_n$—$COOR^3$ wherein $R^3$ is a $C_1$ to $C_{17}$ hydrocarbon or heterohydrocarbon group, the latter having one or more nitrogen, halogen, or oxygen atoms, and n is an integer of from 1 to 5.

5. The method of claim 1 wherein compound (A) is a cyanoactetate (ii) of formula V and $R^2$ is a $C_1$ to $C_6$ hydrocarbon.

6. The method of claim 1 wherein the equivalent weight of iminium salt to malonic acid ester is from 1:1 to 10:1.

7. The method of claim 1 wherein, an acid halide is present and is an acid chloride.

8. The method of claim 1 wherein the acid halide and/or acid anhydride are selected from the group consisting of acetyl chloride, propionyl chloride, isobutyryl chloride, trimethylacetyl chloride, acetic anhydride, propionic anhydride, isobutyric anhydride, trimethylacetic anhydride, trifluoro anhydride, sulfonic acid anhydride, benzoyl chloride, chloroacetylchloride.

9. The method of claim 1 wherein the reaction is conducted in the presence of a non-polar solvent.

10. The method of claim 9 wherein the non-polar solvent is selected from the group consisting of toluene, benzene, diethylether, chloroform, hexane, cyclohexane and carbontetrachloride.

* * * * *